United States Patent [19]

Shepard

[11] Patent Number: 4,486,444
[45] Date of Patent: Dec. 4, 1984

[54] (HYDROXYBENZOYL)THIOPHENESULFONAMIDE AND ACYL DERIVATIVES THEREOF FOR THE TOPICAL TREATMENT OF ELEVATED INTRAOCULAR PRESSURE

[75] Inventor: Kenneth L. Shepard, North Wales, Pa.

[73] Assignee: Merck & Co., Inc., Rahway, N.J.

[21] Appl. No.: 505,604

[22] Filed: Jun. 20, 1983

[51] Int. Cl.³ .................. A61K 31/38; A61K 31/435; C07D 333/16; C07D 211/68
[52] U.S. Cl. .................................. 424/275; 424/256; 424/263; 424/267; 424/274; 549/59; 549/60; 549/64; 546/193; 546/208; 546/212; 546/280; 544/124; 544/146; 548/527
[58] Field of Search .............................. 549/64, 59, 60; 424/275, 263, 267, 256, 274; 546/280, 193, 208, 212; 544/124, 146; 548/527

[56] References Cited

U.S. PATENT DOCUMENTS 4,386,098  5/1983  Woltersdorf et al. .............. 424/270

FOREIGN PATENT DOCUMENTS 1468111  10/1975  United Kingdom .

Primary Examiner—Alan Siegel
Attorney, Agent, or Firm—William H. Nicholson

[57] ABSTRACT (Hydroxybenzoyl)thiophenesulfonamide and acyl derivatives thereof are useful for the topical treatment of elevated intraocular pressure in ophthalmic compositions including drops and inserts.

13 Claims, No Drawings

(HYDROXYBENZOYL)THIOPHENESULFONAMIDE AND ACYL DERIVATIVES THEREOF FOR THE TOPICAL TREATMENT OF ELEVATED INTRAOCULAR PRESSURE

SUMMARY OF THE INVENTION

This invention relates to (hydroxybenzoyl)thiophenesulfonamide and novel acyloxy derivatives thereof which are useful in the treatment of elevated intraocular pressure. More particularly this invention relates to compounds having the structural formula:

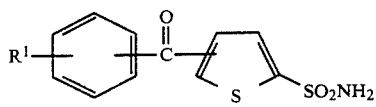

wherein $R^1$ is as hereinafter defined, and the ophthalmologically acceptable salts thereof. This invention also relates to ophthalmic compositions that are employed in the treatment of elevated intraocular pressure, especially when accompanied by pathological damage such as in the disease known as glaucoma.

BACKGROUND OF THE INVENTION

Glaucoma is an ocular disorder associated with elevated ocular pressures which are too high for normal function and may result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by many ophthalmologists to represent the earliest phase of glaucoma.

Many of the drugs formerly used to treat glaucoma proved not entirely satisfactory. Indeed, few advances were made in the treatment of glaucoma since pilocarpine and physostigmine were introduced. Only recently have clinicians noted that many β-adrenergic blocking agents are effective in reducing intraocular pressure. While many of these agents are effective in reducing intraocular pressure, they also have other characteristics, e.g. membrane stabilizing activity, that are not acceptable for chronic ocular use.

(S)-1-tert-butylamino-3-[(4-morpholino-1,2,5-thiadiazol-3-yl)oxy]-b 2-propanol, a β-adrenergic blocking agent, was found to reduce intraocular pressure and to be devoid of many unwanted side effects associated with pilocarpine and, in addition, to possess advantages over many other β-adrenergic blocking agents, e.g. to be devoid of local anesthetic properties, to have a long duration of activity, and to display minimal tolerance.

Although pilocarpine, physostigmine and β-blocking agents reduce intraocular pressure, none of these drugs manifests its action by inhibiting the enzyme carbonic anhydrase and, thereby, impeding the contribution made by the carbonic anhydrase pathway to aqueous humor formation.

Agents referred to as carbonic anhydrase inhibitors, block or impede this inflow pathway by inhibiting the enzyme, carbonic anhydrase. While such carbonic anhydrase inhibitors are now used to treat intraocular pressure by oral, intravenous or other systemic routes, they thereby have the distinct disadvantage of inhibiting carbonic anhydrase throughout the entire body. Such a gross disruption of a basic enzyme system is justified only during an acute attack of alarmingly elevated intraocular pressure, or when no other agent is effective. Despite the desireability of directing the carbonic anhydrase inhibitor only to the desired ophthalmic target tissue, no topically effective carbonic anhydrase inhibitors are available for clinical use.

DETAILED DESCRIPTION OF THE INVENTION

A preferred embodiment of the novel compounds of this invention has structural formula:

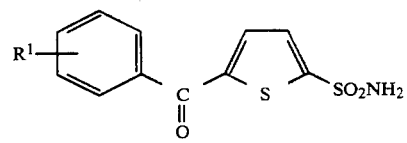

or a pharmaceutically acceptable salt thereof, wherein $R^1$ is HO— or

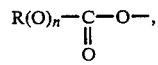

wherein
n is 0 or 1;
R is
(1) $C_{1-18}$alkyl, either straight or branched chain,
(2) $C_{1-18}$ haloalkyl, wherein halo is chloro, bromo, or fluoro,
(3) $R^2R^2N$—$C_{1-5}$alkyl, wherein $R^1$ and $R^2$ are independently hydrogen or $C_{1-3}$alkyl, or $R^1$ and $R^2$ are joined together to form a heterocycle selected from piperidinyl, morpholinyl, or pyrrolidinyl,
(4) $C_{1-3}$alkoxycarbonyl-$C_{1-5}$alkyl,
(5) $C_{3-6}$cycloalkyl,
(6) $C_{3-6}$cycloalkyl-$C_{1-3}$alkyl,
(7) $C_{1-3}$alkyl-$C_{3-6}$cycloalkyl,
(8) aryl, wherein aryl is a carbocycle or heterocycle such as phenyl, naphthyl, pyridinyl, furanyl, thienyl, or the like, either unsubstituted or substituted with one or more of $C_{1-3}$alkyl, halo or $C_{1-3}$alkoxy,
(9) aryl-$C_{1-3}$alkyl, either unsubstituted or substituted with one or more of halo, $C_{1-3}$alkyl or $C_{1-3}$alkoxy,
(10) $C_{2-6}$alkenyl,
(11) $C_{2-6}$alkynyl,
(12) aryl-$C_{2-6}$alkenyl,
(13) $NR^3$-piperidinyl, wherein $R^3$ is $C_{1-3}$alkyl or $C_{2-5}$alkanoyl, or
(14) $C_{1-3}$alkoxy-$C_{1-5}$alkyl.

Representative novel compounds of this invention include those wherein the substituent group, $R^1$ representing HO— or

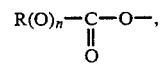

is in the 3 or 4 position of the phenyl group and R represents: phenyl, ethyl, propyl, 1,1-dimethylethyl, heptyl, undecanyl, 4,4-dimethylcyclohexyl; 2-chloro-1,1-dimethylethyl; 4-methylphenyl; 4-chlorophenyl; 4-methoxyphenyl; 4-chlorobenzyl; 3-(4-ethylphenyl)ethyl; allyl; 2-propynyl; 3-phenylallyl; cyclopentylmethyl; benzyl; cyclohexyl; methyl; 1,1-dimethyl-2-dimethylaminoethyl; 2-(methoxycarbonyl)ethyl; 4-(1-acetylpiperidinyl); and 3-pyridyl.

Especially preferred are the compounds wherein $R^1$ is HO— or

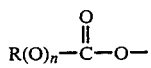

wherein R is $C_{1-18}$ alkyl and most particularly preferred are those compounds wherein $R^1$ is HO— or

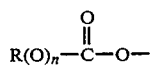

wherein R is $C_{1-5}$ alkyl, either straight or branched chain.

It is also preferred that the $R^1$ group be in the 4-position of the phenyl.

The novel compound wherein $R^1$ is HO— is prepared by heating the compound of structure:

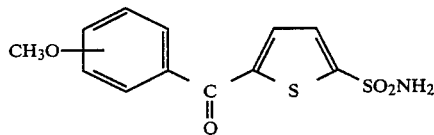

in admixture with pyridine hydrochloride between its fusion point and about 250° C., preferably at about 200° C., for about 15 minutes to about 2 hours.

The compounds of this invention wherein $R^1$ is

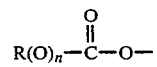

are most suitably prepared by reacting a compound of formula:

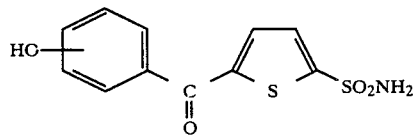

with a compound of the formula:

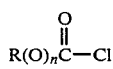

or a bis carbonate of the formula:

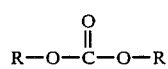

for those compounds wherein n=1, or an anhydride of formula:

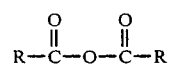

for those compounds wherein n is 0.

The reaction is conducted in a suitable solvent such as dimethylformamide, pyridine, acetone, ethyl acetate, tetrahydrofuran or benzene and the like with at least an equimolar amount of a hydrohalide acceptor. Bases such as triethylamine, pyridine and the like may be employed for this purpose.

The reaction may be conducted with or without a catalyst at temperatures of from 0° C. to the boiling point of the solvent used but preferably from 15° C. to 50° C.

When a catalyst is employed, triethylamine or a 4,4-dialkylaminopyridine such as 4-dimethylaminopyridine or 4-pyrrolidinopyridine is preferred.

The following examples describe the general preparative methods employed.

EXAMPLE 1

Preparation of 5-(4-Hydroxybenzoyl)thiophene-2-sulfonamide

Step A: Preparation of 2-Bromo-5-(4-methoxybenzoyl)thiophene

To a cold (0°–5° C.) solution of 2-bromothiophene (32.6 g, 0.2 mol) and p-methoxybenzoyl chloride (34.1 g, 0.2 mol) in methylene chloride was added anhydrous stannic chloride (52 g, 0.2 mol) dropwise over about one hour. When addition was complete, the cooling bath was removed and the solution was stirred for an additional two hours. A solution of water (90 mL) and concentrated hydrochloric acid (10 mL) was added dropwise and the layers were separated. The organic layer was washed with water, saturated sodium chloride solution and dried ($MgSO_4$). Removal of the solvent in vacuo and collection of the slide with the aid of hexane gave 48.5 g, of gray powder, m.p. 97°–99° C. A sample was recrystallized from ligroin for analysis.

(Anal. Calc'd for $C_{12}H_9BrO_2S$: C, 48.50; H, 3.05. Found: C, 49.11; H, 3.00.

Step B: Preparation of 2-Benzylmercapto-5-(4-methoxybenzoyl)thiophene

Benzyl mercaptan (1.24 g, 0.01 mol) was added to a stirred mixture of sodium hydride (50% oil dispersion, 0.44 g, 0.11 mol) and degassed DMF (10 mL). The resulting mixture was warmed cautiously until gas evolution ceased. After cooling to 25° C., a solution of 2-bromo-5-(4-methoxybenzoyl)thiophene (2.97 g, 0.01 mol) in DMF (10 mL) was added dropwise. After complete addition, the mixture was heated on the steam bath for 2.5 hours and poured into waTER (200 mL). The aqueous mixture was extracted with ether (2×200 mL) and the extracts were washed with water, saturated NaCl solution and dried ($Na_2SO_4$). After evaporation of the solvent, the residue was collected with the aid of hexane and dried, 1.98 g, m.p. 103°–105° C.

Anal. Calc'd. for $C_{19}H_{16}O_2S_2$: C, 67.03; H, 4.74. Found: C, 67.19; H, 4.64.

Step C: Preparation of 5-(4-Methoxybenzoyl)thiophene-2-sulfonamide

Chlorine was bubbled into a stirred cold (0°–10° C.) mixture of 2-benzylmercapto-5-(4-methoxybenzoyl)thiophene (3.4 g) and 33% aqueous acetic acid (50 mL). When the temperature no longer rose during the addition (ca. 20 min.), the pale yellow solid was filtered, washed well with water then hexane. The resulting solid was dissolved in acetone (50 mL) and added to cold (0°–5° C.) concentrated aqueous ammonia (100 ml). The mixture was stirred 16–24 hours (25° C.) and diluted with water. The solid that separated was collected and recrystallized from 95% ethanol, m.p. 176°–178° C.

Anal. Calc'd. for $C_{12}H_{11}NO_4S_2$: C, 48.47; H, 3.73; N, 4.71. Found: C, 48.20; H, 3.70; N, 4.74.

Step D: Preparation of 5-(4-Hydroxybenzoyl)thiophene-2-sulfonamide

A mixture of 5-(4-methoxybenzoyl)thiophene-2-sulfonamide (5.48 g) and pyridine hydrochloride (50 g.) was heated to 200° C. for 0.5 hour. Water (400 mL) was added to the cooled reaction mixture and the solid collected by filtration. This solid was stirred with 1N hydrochloric acid (100 mL) for 0.5 hour, filtered, washed with water and dried at 70° C., 4.11 g, m.p. 183°–190° C. Treatment of this material with acetonitrile, followed by sodium bicarbonate solution then 3N hydrochloric acid, and recrystallization from water gave 1.70 g, m.p. 200°–201° C.

Anal. Calc'd for $C_{11}H_9NO_4S_2$: C, 46.63; H, 3.20; N, 4.94. Found: C, 46.63; H, 3.13; N, 4.94.

EXAMPLE 2

4-[(2-Sulfamoyl-5-thienyl)carbonyl]phenyl 2,2-Dimethylpropionate

A solution of 5-(4-hydroxybenzoyl)thiophene-2-sulfonamide (0.01459 mole) in acetone (90 ml) at 0° C. is treated with triethylamine (0.0160 mole) and 4-dimethylaminopyridine (75 mg). Trimethylacetic anhydride (0.0160 mole) is added, dropwise, during 20 minutes at 0° C. The cooling bath is removed and stirring is continued for 1 hour. The acetone is removed in vacuo and the residue is dissolved in ethyl acetate, washed with water and saturated sodium chloride solution and dried over sodium sulfate. The ethyl acetate is evaporated in vacuo to give the title compound.

Employing the procedure substantially as described in Example 2, but substituting for the anhydride used in Example 2, an equimolar amount of the reagent of formula

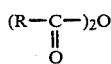

described in Table I, there are produced the acyloxy compounds also described in Table I in accordance with the following reaction:

TABLE I

| R | R |
|---|---|
| phenyl, | 3-phenyl-2-propenyl, |
| ethyl, | cyclopentylmethyl, |
| propyl, | benzyl, |
| n-heptyl, | cyclohexyl, |
| n-undecanyl | 2,2-dimethylpropyl, |
| 4,4-dimethylcyclohexyl, | cinnamyl, |
| 2-chloro-1,1-dimethylethyl, | 4-pyridylmethyl, |
| 4-methylphenyl, | cyclopentyl |
| 4-chlorophenyl, | 2,2,2-trifluoroethyl, |
| 4-methoxyphenyl, | 2-propynyl, |
| 4-chlorobenzyl, | 1,1-dimethyl-2-dimethyl- |
| 2-(4-ethylphenyl)ethyl, | aminoethyl, |
| allyl, | 2-methoxycarbonylethyl, |
| 1-acetyl-4-piperidyl, | methyl |
| 3-pyridyl | |

EXAMPLE 3

2-Methylpropyl 4-[(2-Sulfamoyl-5-thienyl)carbonyl]phenyl Carbonate

A solution of 5-(4-hydroxybenzoyl)thiophene-2-sulfonamide (0.00783 mole) in acetone (50 ml) at 0° C. is treated with triethylamine (0.00861 mole) followed by isobutyl chloroformate (0.00861 mole) dropwise, during 30 minutes at 0°–2° C.

After 15 additional minutes, triethylamine hydrochloride is removed by filtration and the filtrate is evaporated in vacuo to give the title compound.

Employing the procedure substantially as described in Example 3, but substituting for the chloroformate used in Example 2 an equimolar amount of the reagent of formula

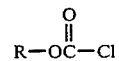

described in Table II there are prepared the carbonates also described in Table II in accordance with the following reaction:

TABLE II

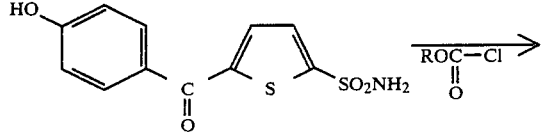

| R | R |
|---|---|
| phenyl, | 3-phenyl-2-propenyl, |
| propyl, | cyclopentylmethyl, |
| propyl, | benzyl, |
| n-heptyl, | cyclohexyl, |
| n-undecanyl | methyl, |
| 4,4-dimethylcyclohexyl, | 2,2-dimethylpropyl, |
| 2-chloro-1,1-dimethylethyl, | cinnamyl, |
| 4-methylphenyl, | 4-pyridylmethyl, |
| 4-chlorophenyl, | cyclopentyl |
| 4-methoxyphenyl, | 4-nitrophenyl, |
| 4-chlorobenzyl, | 2-(triphenylphosphonium)- |
| 2-(4-ethylphenyl)ethyl, | ethyl, |
| allyl, | 2,2,2-trifluoroethyl, |
| 2-propynyl, | |

Using the methods of Examples 2 and 3, but substituting the appropriate starting materials the entire range of the compounds wherein R is as defined can be prepared.

For use in treatment of conditions relieved by the inhibition of carbonic anhydrase, the active compound can be administered either systemically, or, in the treatment of the eye, topically. The dose administered can be from as little as 0.1 to 25 mg or more per day, singly, or preferably on a 2 to 4 dose per day regimen although a single dose is satisfactory.

When administered for the treatment of elevated intraocular pressure of glaucoma, the active compound is most desireably administered topically to the eye, although systemic treatment is also satisfactory.

When given systemically, the drug can be given by any route, although the oral route is preferred. In oral administration the drug can be employed in any of the usual dosage forms such as tablets or capsules, either in a contemporaneous delivery or sustained release form. Any number of the usual excipients or tableting aids can likewise be included.

The active drug of this invention is most suitably administered in the form of ophthalmic pharmaceutical compositions adapted for topical administration to the eye such as a suspension, ointment, or as a solid insert. Formulations of these compounds may contain from 0.01 to 15% and especially 0.5% to 3% of medicament. Higher dosages as, for example, about 10%, or lower dosage can be employed provided the dose is effective in reducing or controlling elevated intraocular pressure. As a unit dosage from between 0.001 to 10.0 mg, preferably 0.005 to 2.0 mg, and especially 0.1 to 1.0 mg of the compound is generally applied to the human eye, generally on a daily basis in single or divided doses so long as the condition being treated exists.

These hereinbefore described dosage values are believed accurate for human patients and are based on the known and presently understood pharmacology of the compounds, and the active of other similar entities in the human eye. They reflect the best mode known. As with all medications, dosage requirements are variable and must be individualized on the basis of the disease and the response of the patient.

The pharmaceutical preparation which contains the active compound may be conveniently admixed with a non-toxic pharmaceutical organic carrier, or with a non-toxic pharmaceutical inorganic carrier. Typical of pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethylcellulose, polyvinylpyrrolidone, isopropyl myristrate and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetracetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like. The pharmaceutical preparation may also be in the form of a solid insert.

While many patients find liquid medication to be entirely satisfactory, others may prefer a solid medicament that is topically applied to the eye, for example, a solid dosage form that is suitable for insertion into the cul-de-sac. To this end the carbonic anhydrase inhibiting agent can be included with a non-bioerodible insert, i.e. one which after dispensing the drug remains essentially intact, or a bioerodible insert, i.e. one that either is soluble in lacrimal fluids, or otherwise disintegrates. While the insert employed is not critical and those disclosed in U.S. Pat. Nos. 3,630,200 Higuchi; 3,811,444 Heller et al.; 4,177,256 Michaels et al.; 3,868,445 Ryde et al.; 3,845,201 Haddad; 3,981,303 Higuchi; and 3,867,519 Michaels, are satisfactory; in general, however, the insert described below is found preferable.

For example, one may use a solid water soluble polymer as the carrier for the medicament. The polymer used to form the insert may be any water soluble non-toxic polymer, for example, cellulose derivatives such as methylcellulose, sodium carboxymethyl cellulose, or a hydroxy lower alkyl cellulose such as hydroxyethyl cellulose, hydroxypropyl cellulose, hydroxypropylmethyl cellulose and the like; acrylates such as polyacrylic acid salts, ethyl acrylates, polyacrylamides; natural products such as gelatin, alginates, pectins, tragacanth, karaya, chondrus, agar, acacia; the starch derivatives such as starch acetate, hydroxyethyl starch ethers, hydroxypropyl starch, as well as other synthetic derivatives such as polyvinyl alcohol, polyvinyl pyrrolidone, polyvinyl methyl ether, polyethylene oxide, neutralized carbopol and xanthan gum, and mixtures of said polymer.

The following examples of ophthalmic formulations are given by way of illustration.

EXAMPLE 4

| Solution Composition | | |
|---|---|---|
| 2-Methylpropyl 4-[(2-Sulfamoyl-5-thienyl)carbonyl]phenyl Carbonate | 1 mg | 15 mg. |
| Monobasic sodium phosphate .2H$_2$O | 9.38 mg. | 6.10 mg. |
| Dibasic sodium phosphate .12H$_2$O | 28.48 mg | 16.80 mg. |
| Benzalkonium chloride | 0.10 mg. | 0.10 mg. |
| Water for injection q.s. ad. | 1.0 ml. | 1.0 ml. |

The sterile components are added to and suspended in sterile water. The pH of the suspension is adjusted to 6.8 sterilely and diluted to volume.

EXAMPLE 5

| | |
|---|---|
| 4-[(2-Sulfamoyl-5-thienyl)carbonyl]phenyl Nicotinate | 5 mg. |
| petrolatum q.s. ad. | 1 gram |

Compound I and the petrolatum are aseptically combined.

EXAMPLE 6

| | |
|---|---|
| 4-[(2-Sulfamoyl-5-thienyl)carbonyl]phenyl Acetate | 1 mg. |
| Hydroxypropylcellulose q.s. | 12 mg. |

Ophthalmic inserts are manufactured from compression molded films which are prepared on a Carver Press by subjecting the powdered mixture of the above ingredients to a compressional force of 12,000 lbs. (gauge) at 300° F. for one to four minutes. The film is cooled under pressure by having cold water circulate in the platen. Ophthalmic inserts are then individually cut from the film with a rod-shaped punch. Each insert is placed into a vial, which is then placed in a humidity cabinet (88% R.H. at 30° C.) for two to four days. After removal from the humidity cabinet, the vials are stoppered and then capped. The vials containing the hydrate insert are then autoclaved at 250° F. for ½ hour.

EXAMPLE 7

| | |
|---|---|
| 4-[(2-Sulfamoyl-5-thienyl)carbonyl]phenyl 2,2-Dimethylpropionate | 1 mg. |
| Hydroxypropyl cellulose q.s. ad. | 12 mg. |

Ophthalmic inserts are manufactured from a solent cast film prepared by making a viscous solution of the powdered ingredients listed above using methanol as the solvent. The solution is placed on a Teflon plate and allowed to dry at ambient conditions. After drying, the film is placed in an 88% R. H. cabinet until it is pliable. Appropriately sized inserts are cut from the film.

EXAMPLE 8

| | |
|---|---|
| 4-[(2-Sulfamoyl-5-thienyl)carbonyl]phenyl 2,2-Dimethyl-3-dimethylaminopropionate | 1 mg. |
| Hydroxypropyl methyl cellulose q.s. ad. | 12 mg. |

Ophthalmic inserts are manufactured from a solent cast film which is prepared by making a viscous solution of the powdered blend of the above ingredients using a methanol/water solvent system (10 ml. methanol is added to 2.5 g. of the powdered blend, to which 11 ml. of water (in three divided portions) is added. The solution is placed on a Teflon plate and allowed to dry at ambient conditions. After drying, the film is placed in an 88% R. H. cabinet until it is pliable. Appropriately sized inserts are then cut from the film.

EXAMPLE 9

| | |
|---|---|
| 4-[(2-Sulfamoyl-5-thienyl)carbonyl]phenyl 3-(Methoxycarbonyl)propionate | 1 mg. |
| Hydroxypropylmethyl cellulose q.s. ad. | 12 mg. |

It is highly preferred that the solid inserts of this invention are available for use by the patient in a pathogen free condition. Thus, it is preferred to sterilize the inserts and so as insure against recontamination, the sterilization is preferably conducted after packaging. The best mode of sterilizing is to employ ionizing irradiation including irradiation emanating from Cobalt 60 or high energy electron beams.

The following examples illustrate preparation of the improved ophthalmic suspension compositions of the present invention.

EXAMPLE 10

The following materials are admixed in a 1250 ml bottle: 24 g of 2-methylpropyl 4-[(2-sulfamoyl-5-thienyl)carbonyl]phenyl carbonate which is a sufficient amount of medicament to result in a concentration of 10 mg per ml in the final samples, allowing for previously established 3.0% average; 0.4 g sodium bisulfite, 12 g NaCl, and 28 ml water (at 180° F.) This mixture, (I), is autoclaved for 30 minutes at 121° C. under 15 psig. Separately, 3 g of hydroxyethylcellulose in 720 ml of water (II) and 0.4 g of lecithin in 80 ml of water (III) were autoclaved for 30 minutes at 121° C. Then, (III) is admixed with (I) for 2 hours, and the resultant mixture poured into (II). Another mixture (IV) is prepared from 20 g of sorbitol, 2.36 ml of benzalkonium chloride, 10 g of disodium edetate, and water to give a final solution volume of 900 ml. Then, (IV) is added to the mixture of (I), (II), and (III) in sufficient quantity to give 1.8 l. overall. The 1.8 l. mixture of I, II, III, and IV is then taken and homogenized using a homogenizer at 2000 psig. Stock Solutions are then prepared for polyoxyethylene (20) sorbitan monooleate by dissolving 3 g of the material in 100 ml of water, and of benzyl alcohol/β-phenyl-ethyl alcohol by admixing 50 ml of each alcohol. Varying quantities of the two stock solutions are then added to four 90 ml aliquots of the homogenized mixture of (I), (II), (III), and (IV) prepared as described above, together with sufficient water to give a total of 100 ml for each of four different samples.

Other formulations, in an oil vehicle and an ointment are exemplified in the following examples.

EXAMPLE 11

| | |
|---|---|
| 2-Methylpropyl 4-[(2-Sulfamoyl-5-thienyl)carbonyl]phenyl Carbonate | 0.1 mg. |
| Peanut oil q.s. ad. | 0.10 mg. |

EXAMPLE 12

| | |
|---|---|
| 4-[(2-Sulfamoyl-5-thienyl)carbonyl]phenyl 2,2-Dimethylpropionate | 0.5 gm. |
| Petrolatum q.s. ad. | 1 gram |

The active principal and the petrolatum are aseptically combined

What is claimed is:

1. A compound of structural formula:

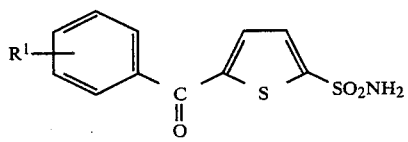

or a pharmaceutically acceptable salt thereof, wherein $R^1$ is HO— or

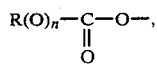

wherein
n is 0 or 1;
R is
(1) $C_{1-18}$alkyl, either straight or branched chain,
(2) $C_{1-18}$haloalkyl, wherein halo is chloro, bromo, or fluoro,
(3) $R^1R^2N$—$C_{1-5}$alkyl, wherein $R^1$ and $R^2$ are independently hydrogen or $C_{1-3}$alkyl, or $R^1$ and $R^2$ are joined together to form a heterocycle selected from piperidinyl, morpholinyl, or pyrrolidinyl,
(4) $C_{1-3}$alkoxycarbonyl-$C_{1-5}$alkyl,
(5) $C_{3-6}$cycloalkyl,
(6) $C_{3-6}$cycloalkyl-$C_{1-3}$alkyl,
(7) $C_{1-3}$alkyl-$C_{3-6}$cycloalkyl,
(8) aryl, wherein aryl is a carbocycle or heterocycle selcted from phenyl, naphthyl, pyridinyl, furanyl or thienyl, either unsubstituted or substituted with one or more of $C_{1-3}$alkyl, halo or $C_{1-3}$alkoxy,
(9) aryl-$C_{1-3}$alkyl, either unsubstituted or substituted with one or more of halo, $C_{1-3}$alkyl or $C_{1-3}$alkoxy,
(10) $C_{2-6}$alkenyl,
(11) $C_{2-6}$alkynyl,
(12) aryl-$C_{2-6}$alkenyl,
(13) $NR^3$-piperidinyl, wherein $R^3$ is $C_{1-3}$alkyl or $C_{2-5}$alkanoyl, or
(14) $C_{1-3}$alkoxy-$C_{1-5}$ alkyl.

2. The compound according to claim 1 wherein $R^1$ is HO— or

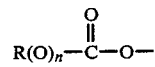

wherein R is $C_{1-18}$ alkyl and is a 4-substituent.

3. The compound according to claim 2 wherein R is $C_{1-15}$ alkyl.

4. A method for treating glaucoma and ocular hypertension and for lowering intraocular pressure which comprises topically applying to an affected eye an effective intraocular pressure lowering amount of the compound of claim 1.

5. The method of claim 4 wherein $R^1$ is HO— or

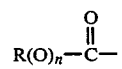

wherein R is $C_{1-18}$alkyl and is a 4-substituent.

6. The method of claim 5 wherein R is $C_{1-5}$alkyl.

7. An ophthalmic composition for the topical treatment of glaucoma and ocular hypertension comprising an intraocular pressure lowering effective amount of the compound of claim 1 and an ophthalmologically acceptable carrier.

8. The composition claim 7 wherein $R^1$ is HO— or

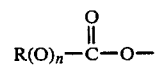

wherein R is $C_{1-18}$alkyl and is a 4-substituent.

9. The composition of claim 8 wherein R is $C_{1-5}$ alkyl.

10. The composition of claim 7 which is a water soluble polymeric insert.

11. The composition of claim 10 wherein the polymer is hydroxypropylcellulose, or polyvinyl alcohol.

12. The composition of claim 7 which is an ointment.

13. The composition of claim 7 wherein the compound is in a liquid vehicle.

* * * * *